United States Patent
Fjeldså

(10) Patent No.: US 10,085,898 B2
(45) Date of Patent: Oct. 2, 2018

(54) ABSORBENT ARTICLE HAVING A MULTI LAYERED SIDE SEAM, AND CORRESPONDING MANUFACTURING METHOD

(75) Inventor: Patrik Fjeldså, Träslövsläge (SE)

(73) Assignee: SCA Hygiene Products AB, Gothenburg (SE)

( * ) Notice: Subject to any disclaimer, the term of this patent is extended or adjusted under 35 U.S.C. 154(b) by 957 days.

(21) Appl. No.: 14/395,899

(22) PCT Filed: May 8, 2012

(86) PCT No.: PCT/EP2012/058440
§ 371 (c)(1),
(2), (4) Date: Oct. 21, 2014

(87) PCT Pub. No.: WO2013/167170
PCT Pub. Date: Nov. 14, 2013

(65) Prior Publication Data
US 2015/0080820 A1    Mar. 19, 2015

(51) Int. Cl.
*A61F 13/15* (2006.01)
*A61F 13/20* (2006.01)
(Continued)

(52) U.S. Cl.
CPC ........ *A61F 13/56* (2013.01); *A61F 13/15699* (2013.01); *A61F 13/15723* (2013.01);
(Continued)

(58) Field of Classification Search
CPC combination set(s) only.
See application file for complete search history.

(56) References Cited

U.S. PATENT DOCUMENTS

| 4,693,771 A * | 9/1987 | Payet ..................... B26D 7/086 |
| | | 156/73.3 |
| 5,607,537 A * | 3/1997 | Johnson ............ A61F 13/15699 |
| | | 156/157 |

(Continued)

FOREIGN PATENT DOCUMENTS

WO  WO 2005/122984 A1   12/2005
WO  WO 2005/122985 A1   12/2005
(Continued)

OTHER PUBLICATIONS

International Search Report (PCT/ISA/210) dated Mar. 4, 2013, by the European Patent Office as the International Searching Authority for International Application No. PCT/EP2012/058440.
(Continued)

*Primary Examiner* — Michele M Kidwell
(74) *Attorney, Agent, or Firm* — Buchanan Ingersoll & Rooney PC

(57) ABSTRACT

An absorbent article, such as a pant diaper, a sanitary pant or an incontinence pant, includes a front part, a back part, and a crotch part. Lateral side portions of the front part and the back part are superposed, so that their inner surfaces face each other, and are joined to each other along side seams extending in a longitudinal direction of the article. The lateral side portions of the front part and/or the back part include at least one layer of nonwoven material which is reinforced in the area of at least one of the side seams.

11 Claims, 7 Drawing Sheets

(51) Int. Cl.
*A61F 13/56* (2006.01)
*D04H 1/00* (2006.01)

(52) U.S. Cl.
CPC ............ *A61F 13/565* (2013.01); *D04H 1/00* (2013.01); *Y10T 156/10* (2015.01); *Y10T 156/108* (2015.01); *Y10T 156/1051* (2015.01)

(56) References Cited

U.S. PATENT DOCUMENTS

| | | | |
|---|---|---|---|
| 2002/0138063 A1* | 9/2002 | Kuen | A61F 13/15699 604/391 |
| 2006/0271009 A1* | 11/2006 | Cartier | A61F 13/15203 604/385.31 |
| 2008/0114325 A1* | 5/2008 | Edwall | A61F 13/49011 604/385.24 |
| 2009/0107614 A1 | 4/2009 | Cartier et al. | |
| 2010/0063468 A1 | 3/2010 | Lehto et al. | |

FOREIGN PATENT DOCUMENTS

| | | |
|---|---|---|
| WO | WO 2006/093444 A1 | 9/2006 |
| WO | WO 2007/138373 A1 | 12/2007 |
| WO | WO 2008/079061 A1 | 7/2008 |
| WO | WO 2010/110708 A1 | 9/2010 |

OTHER PUBLICATIONS

Written Opinion (PCT/ISA/237) dated Mar. 4, 2013, by the European Patent Office as the International Searching Authority for International Application No. PCT/EP2012/058440.

* cited by examiner

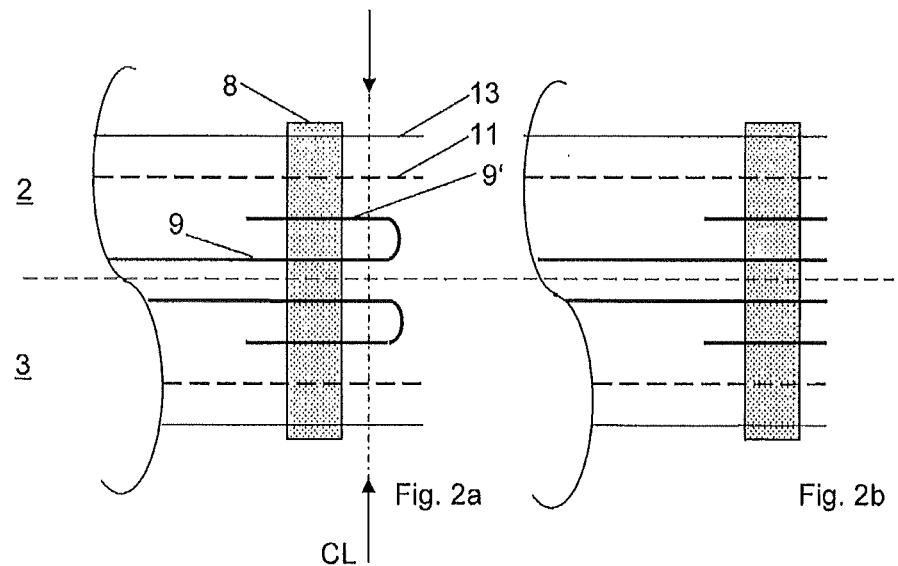
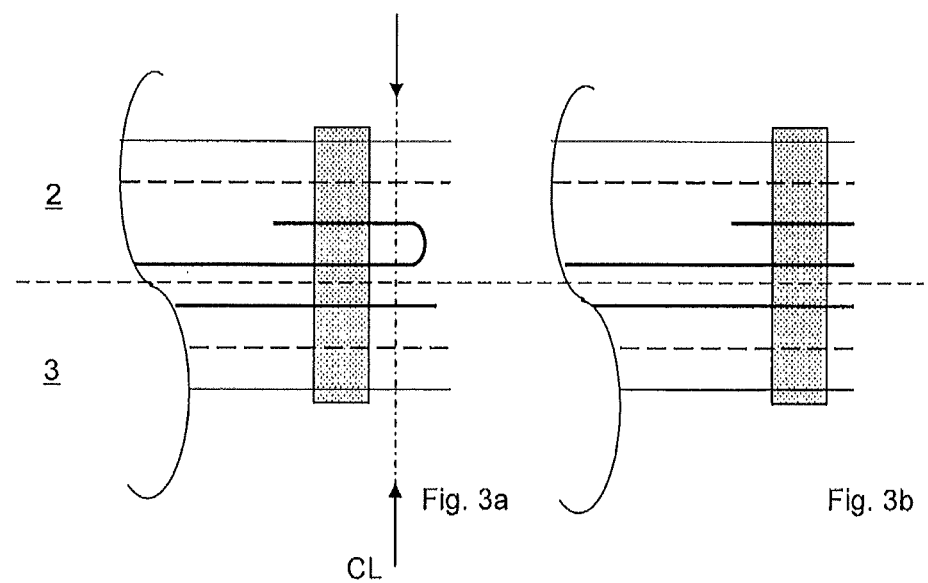

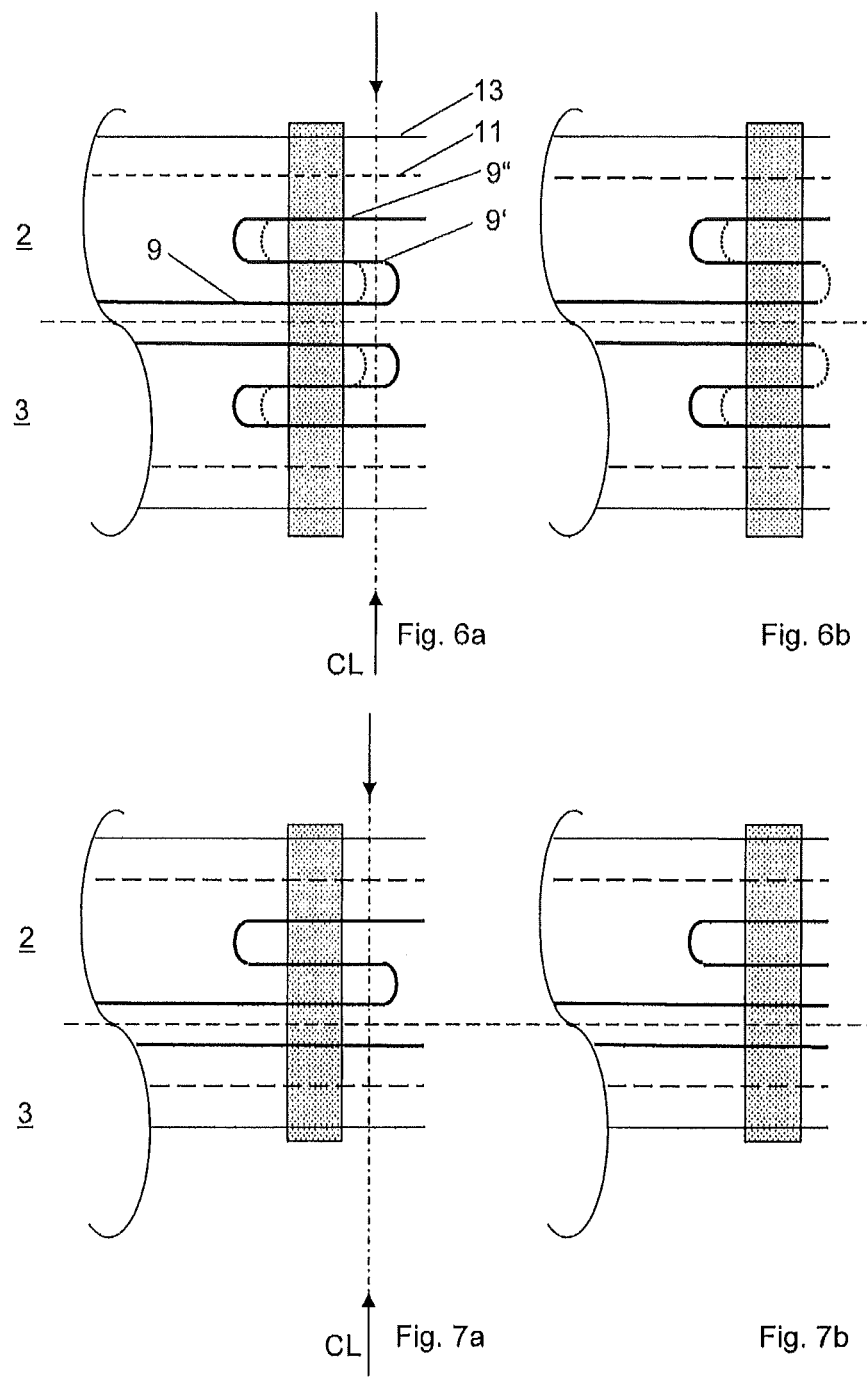

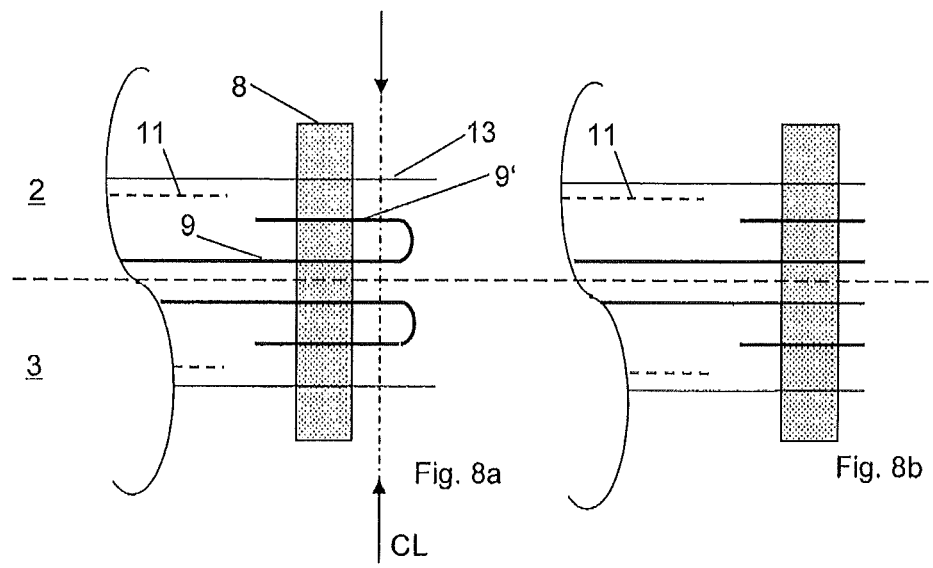
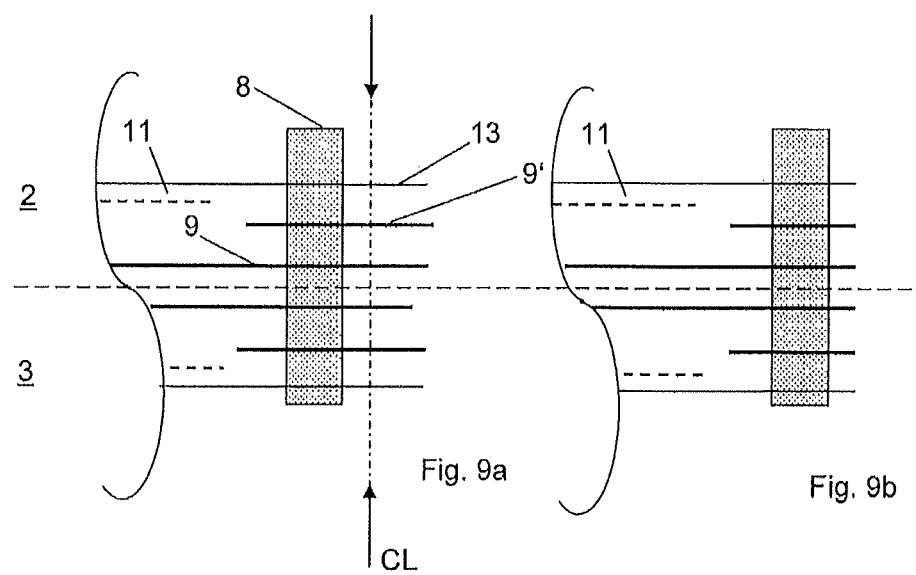

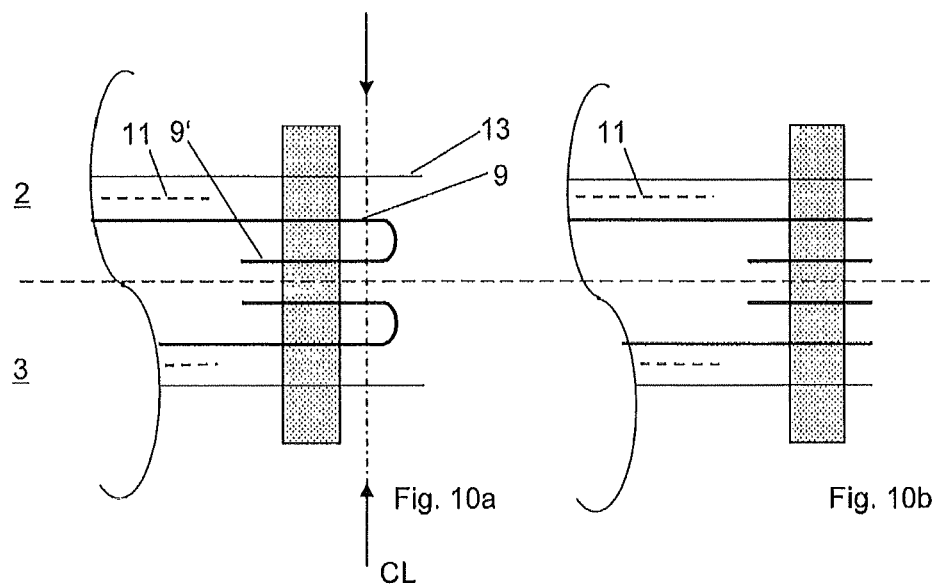
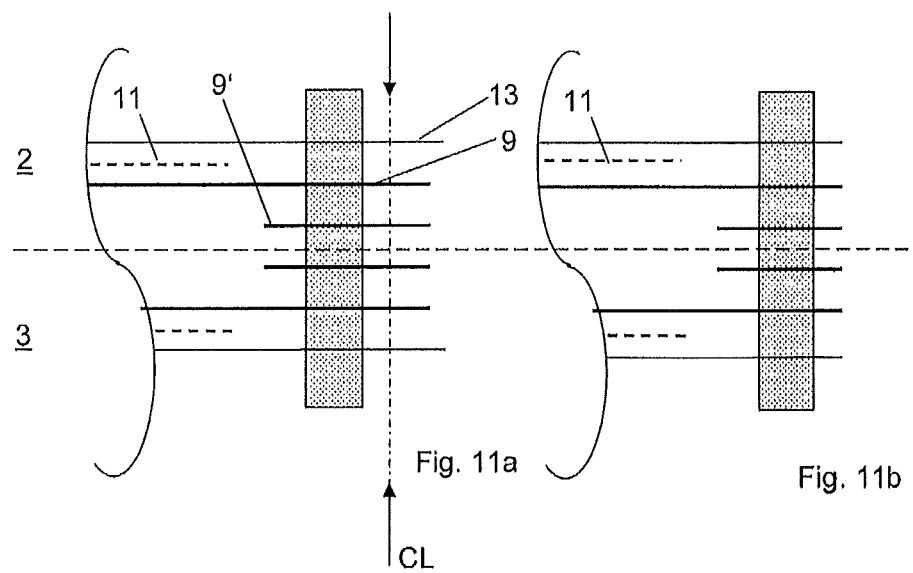

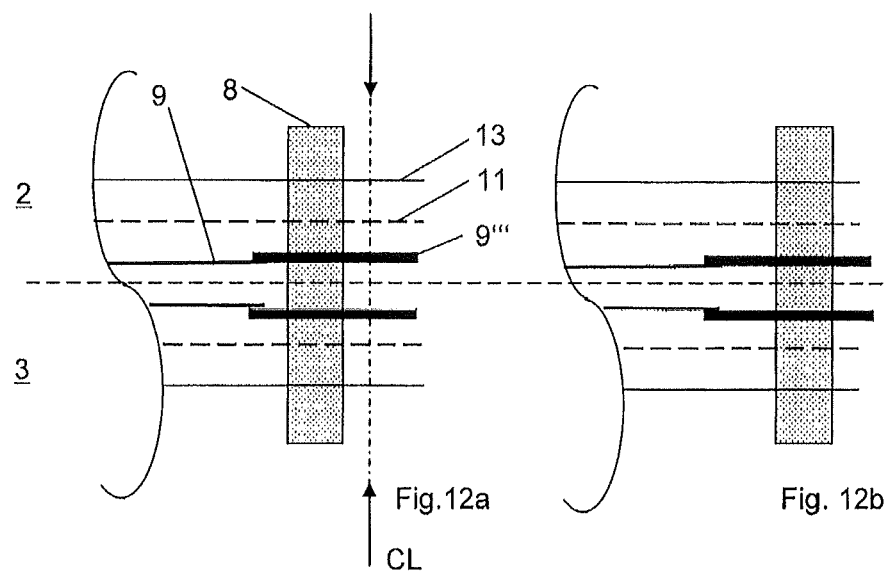
Fig. 12a    Fig. 12b
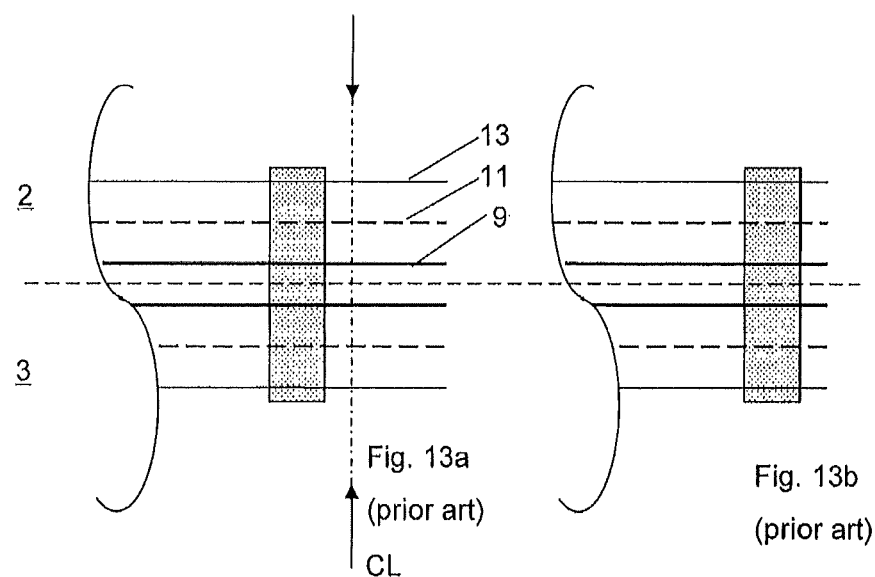
Fig. 13a
(prior art)
Fig. 13b
(prior art)

ABSORBENT ARTICLE HAVING A MULTI LAYERED SIDE SEAM, AND CORRESPONDING MANUFACTURING METHOD

TECHNICAL FIELD

The present disclosure refers to an absorbent article such as a pants-type diaper, a sanitary pant or an incontinence garment, said article comprising a multi layered side seam. The present disclosure further refers to a method of manufacturing such an absorbent article.

BACKGROUND

In the present context, the term "absorbent article" refers to products that are placed against the skin of the wearer to absorb and contain body exudates, like urine, faeces and menstrual fluid. The present disclosure mainly refers to disposable absorbent articles, which means articles that are not intended to be laundered or otherwise restored or reused as an absorbent article after use.

Absorbent articles like pants-type diapers, sanitary pants or incontinence garments are supposed to have a comfortable fit about the wearer. For pants-type absorbent articles it is also desirable that the articles are capable of being pulled up and down over the hips of the wearer to allow the wearer or caregiver to easily put on and remove the article when it has been soiled. There is also a requirement that they should be soft and textile-like. The hygiene pants, in particular for adult users, should be discrete and they should not be bulky, at least in the areas outside the actual absorption unit.

Since they are disposable products, the cost aspect is very important. For cost reasons, the material layers included should be as thin as possible. At the same time, quality and strength requirements should be fulfilled. More particularly, such articles should combine properties of comfort and good fit for the user with strength, so that the article is comfortable to wear, yet its integrity is maintained when it is put on and during use. The hygiene pants, such as diaper pants, should of course resist wear during use. Hygiene pants are exposed to considerable stresses when being put on. Those regions which are most subject to stress, and where failure is most likely to occur, are those regions in which the constitutional elements of the absorbent article are joined together, i.e. the seams of the article. For example, side seams are formed by connecting the respective layers of the front and back parts of the diaper. These seams are commonly formed by welding. The hygiene pants are stretched when they are being pulled over the users' hips, and said seams are exposed to great stresses.

Hygiene pants of the type mentioned at the outset commonly have a cover in the form of an elastic laminate composed of an elastic film applied between two nonwoven layers. The weld seams on this type of elastic laminate are affected, in respect of the strength of the seams, by the material properties and the build-up of the laminate. One object of elastic covers in the form of an elastic film between two nonwoven layers is to give the cover optimal elastic properties at the same time as the fibres in these nonwoven layers give the cover a soft textile feel. The structure of the laminate should therefore be configured such that the desired elastic stretching of the cover is not impeded by the non-woven layers.

International Application WO 2006/093444 A1 discloses disposable hygiene pants comprising elastic web material, in which the side edges (side-seams) which join the front and back parts of the article are welded and reinforced by means of non-woven strips.

SUMMARY

It is the object underlying the present disclosure to provide an absorbent article which can be manufactured in an easy and cost effective manner while providing the desired strength and soft textile feel, as well as a corresponding manufacturing method.

The above object is solved by an absorbent article such as a pant diaper, a sanitary pant or an incontinence pant comprising the features of claim 1.

The article comprises a front part, a back part, and a crotch portion. Lateral side portions of the front part and the back part are superposed, so that their inner surfaces face each other, and joined to each other along side seams extending in a longitudinal direction of the article. In accordance with the present disclosure, the lateral side portions of the front part and/or the back part include at least one layer of nonwoven material which is reinforced in the area of at least one of the side seams.

In the article of the present disclosure, the required seam strength is obtained by reinforcing the non-woven material layer in the area(s) of the side seam(s). Therefore, the nonwoven material layer as such does not need to have a grammage which provides the seam strength already as a single layer. The reduced grammage of the nonwoven material layer leads to a reduction in costs, and the reduced grammage of the nonwoven material layer also leads to the product having a softer feel.

Preferred optional features of the absorbent article are recited in the dependent product claims.

There are several different possibilities for reinforcing the at least one layer of nonwoven material in accordance with the present disclosure. For example, the absorbent article may include at least one additional layer of nonwoven material extending at least in the area of the side seam. A preferred way of obtaining this at least one additional layer of material is by folding the layer of nonwoven material of the lateral side portions of the front and the back part upon itself. The additional layer of material could, however, also be provided by adding a separate strip of nonwoven material in the area of the side seam.

In order to achieve a further reinforcement of the side seam, and/or in order to allow a further reduction of the grammage of the non-woven material layer, the absorbent article may include at least two additional layers of material extending at least in the area of the side seam, which are obtained by double folding the layer of nonwoven material of the lateral side portions of the front part and/or the back part upon itself.

The at least one additional layer of material is preferably provided on the outer surface of the at least one layer of nonwoven material. Since the additional layer of material will then come to be positioned between the nonwoven material layer and at least one further material layer, the additional material layer is not visible in the final product so that the reinforcement of the nonwoven material layer is not immediately apparent from the final product.

Another possibility for reinforcing the at least one non-woven material layer resides in providing said layer with a higher grammage in the area of the side seam. Rather than reinforcing the nonwoven layer by adding an additional layer of material, it is the layer as such which is reinforced upon being thickened. The higher grammage section of the nonwoven layer may be integral with the remainder of the nonwoven layer, or it may be a separate strip which is joined to the edge of the actual nonwoven layer. Alternatively or in addition to increasing the grammage, the strength of the non-woven material layer, in particular the cross directional strength, could be improved in the area of the side seam.

The lateral side portions of the front part and/or the back part of the diaper will often include further material layers in addition to the nonwoven material layer. According to a preferred embodiment, the lateral side portions of the front and back parts include a laminate which is constituted by the at least one layer of nonwoven material and at least one further layer of material. In particular, the laminate may further include an elastic film and/or a further layer of nonwoven material which is then preferably a nonwoven backsheet. According to a suitable arrangement, the laminate includes the layer of nonwoven material, the elastic film and the further layer of nonwoven material (which is preferably the backsheet) which are laminated in this order, wherein the layer of nonwoven material faces the body of the wearer during use. This is, however, only one example, and the present disclosure is not limited to a particular arrangement or order of the layers. The laminate could, for example, also be constituted by only one nonwoven layer and an elastic film.

According to another example, the lateral side portions of the front and/or the back part could further include an elastic film which does, however, not extend in the area(s) where the side seam(s) is/are formed. In the areas of the side seams, the lateral side portions could then include only the nonwoven layers of the front and back parts which are joined to each other and which are reinforced in the areas of the side seams accordance with the present disclosure. As an alternative, both the front and the back part could each have two nonwoven layers in the areas of the side seams, one of which is reinforced in accordance with the present disclosure.

The non-woven material layer may be a standing-gather web, in which standing gathers are formed. The non-woven material layer could also be, for example, a topsheet. In this context, note that in the frame of the present disclosure, the non-woven material layer is a constituent of the lateral side portions of the front part and/or the back part of the article, but this does not mean that the non-woven material layer is exclusively present in these lateral side portions. The non-woven material layer may as well be a layer which extends across the whole of the front part and/or the back part of the diaper. In the case of articles which have separate side panels attached to a chassis, wherein these side panels are connected by means of the side seams, the non-woven material layer would be a constituent of the side panels.

The above object is further solved by a method of manufacturing an absorbent article such as a pants-type diaper, a sanitary pant or an incontinence garment, the method comprising the features of claim 13.

The method includes the steps of:
providing a blank for said article, the blank comprising a front part, a back part, and a crotch portion between the front part and the back part, and
superposing lateral side portions of the front part and the back part, so that their inner surfaces face each other, and joining the lateral side portions of the front and the back part to each other along side seams extending in a longitudinal direction of the article,
wherein, in accordance with the present disclosure, upon superposing the lateral side portions, the lateral side portions of the front part and/or the back part include at least one layer of nonwoven material which has been reinforced beforehand in the area where at least one of the side seam is formed.

Preferred optional features of the manufacturing method are recited in the dependent method claims.

The reinforcing of the layer of nonwoven material may for example be effected by providing the article with at least one additional layer of nonwoven material which extends at least in the area of the side seam.

If so, the said at least one additional layer of nonwoven material is preferably laminated to the layer of nonwoven material prior to the superposing of the lateral side portions of the front part and the back part. The lamination of the additional layer may be only a slight one, since it should merely ensure that the additional layer does not become dislocated from the nonwoven layer during the further handling of the material web. This applies irrespective of whether the additional material layers are obtained by folding the edges of the nonwoven layer, or by inserting a separate layer of material. One possible way of effecting this lamination is by thermomechanical welding. The lamination could, for example, take place at the same stage in which the standing gathers are formed, and by the same bonding method: in case the standing gathers are formed by thermomechanical welding, the additional nonwoven layer is also laminated to the nonwoven layer by thermomechanical welding.

As already explained above in connection with the article, one possibility for obtaining the additional layer of nonwoven material is by folding the layer of nonwoven material of the lateral side portions of the front part and/or the back part upon itself. The folding of the nonwoven material layer upon itself constitutes an easy measure for reinforcing the side seams so as to obtain the required seam strength. The folding of the nonwoven material layer is a process step which can be easily implemented into existing product lines.

In the method of the present disclosure, the layer of nonwoven material of the front part and/or the back part is preferably folded upon itself about a fold line extending essentially in a longitudinal direction of the absorbent article. While the folding about other fold lines would generally be possible, a folding about longitudinal fold lines would be easy to integrate into the manufacturing process and would also make sure that as little material as possible is to be discarded as scrap.

In order to achieve a further reinforcement of the side seam, and/or in order to allow a further reduction of the grammage of the non-woven material layer, the layer of nonwoven material of the lateral side portions of the front part and/or the back part may be double folded upon itself, so as to reinforce the nonwoven layer of the front and/or the back part with two additional layers of material in the area of the side seam.

In order to reinforce the nonwoven material layer in accordance with the present disclosure, the side seam may include at least one additional layer of material which is provided on the side of the outer surface of the at least one layer of nonwoven material. If so, the additional layer of material could be provided by folding, as discussed above, or in another manner.

Alternatively or in addition, the at least one layer of nonwoven material may be reinforced by providing this layer with a higher grammage and/or a higher strength, in particular cross directional (CD) strength, in the area(s) of the side seam(s).

The method may further include the step of providing the lateral side portions of the front and/or the back part with an elastic film which does, however, not extend in the area of the at least one side seam.

One suitable method for forming the side seams is ultrasonic welding.

When ultrasonically welding, the materials to be welded together are worked mechanically by moving the end of an ultrasonic horn up and down, while in contact with the material, with a frequency that lies within the ultrasonic range. Heat is generated in the material as a result of the internal friction created by this mechanical working process, causing the material to melt in the worked area so that materials located in between horn and an opposing anvil will melt and therewith fuse together. Naturally, the heat generated in the materials will depend on the degree to which the material is worked, and if the material is worked to an excessively low degree, the bond between the materials will be weak or non-existent, whereas if the material is worked to an excessive degree, the materials will be perforated.

The anvils are often comprised of projections which stand out from the surface of an anvil holder, so as to provide a small "contact surface" between horn and anvil, and the energy delivered by the welding unit is concentrated over a small area. When welding moving webs of material, the anvils often comprise a suitable pattern of projections on a pattern cylinder or drum.

Forming the side seams by ultrasonic welding provides the advantages that the seams become relatively soft and less stiff than it is the case with other connection methods. The softer the seam, the smaller the probability that the seams will be uncomfortable for the wearer.

As an alternative, the side seams could, however, also be formed by e.g. mechanical or thermo-mechanical welding.

Where the non-woven material layer is a standing-gather web, the method would further include the step of forming standing gathers in the non-woven material layer.

Finally, the method may further including the subsequent step of cutting away parts of the outer longitudinal edge portions of the article beyond the side seams. The outermost parts of the material layers are required for handling and guiding the material during the individual manufacturing process steps, including the welding step. Subsequent to the welding, however, the outermost parts of the material layers may be cut away along a longitudinal cutting line running close to the side seam, so as to provide the resultant article with an appealing appearance. This cutting step is, however, only optional, and dependent on the particular manufacturing method it could as well be that the cutting away of the outermost parts of the material layer can be dispensed with.

BRIEF DESCRIPTION OF THE DRAWINGS

FIGS. 2a and 2b are cross sectional views of a lateral side portion of an absorbent article according to a first embodiment, wherein FIG. 2a shows the lateral side portion in an intermediate manufacturing state of the article, and FIG. 2b shows a final configuration of the lateral side portion.

FIGS. 3a and 3b are cross sectional views of a lateral side portion of an absorbent article according to a second embodiment, wherein FIG. 2a shows the lateral side portion in an intermediate manufacturing state of the article, and FIG. 2b shows a final configuration of the lateral side portion.

FIGS. 4a and 4b are cross sectional views of a lateral side portion of an absorbent article according to a third embodiment, wherein FIG. 4a shows the lateral side portion in an intermediate manufacturing state of the article, and FIG. 4b shows a final configuration of the lateral side portion.

FIGS. 5a and 5b are cross sectional views of a lateral side portion of an absorbent article according to a fourth embodiment, wherein FIG. 5a shows the lateral side portion in an intermediate manufacturing state of the article, and FIG. 5b shows a final configuration of the lateral side portion.

FIGS. 6a and 6b are cross sectional views of a lateral side portion of an absorbent article according to a fifth embodiment, wherein FIG. 6a shows the lateral side portion in an intermediate manufacturing state of the article, and FIG. 6b shows a final configuration of the lateral side portion.

FIGS. 7a and 7b are cross sectional views of a lateral side portion of an absorbent article according to a sixth embodiment, wherein FIG. 7a shows the lateral side portion in an intermediate manufacturing state of the article, and FIG. 7b shows a final configuration of the lateral side portion.

FIGS. 8a and 8b are cross sectional views of a lateral side portion of an absorbent article according to a seventh embodiment, wherein FIG. 8a shows the lateral side portion in an intermediate manufacturing state of the article, and FIG. 8b shows a final configuration of the lateral side portion.

FIGS. 9a and 9b are cross sectional views of a lateral side portion of an absorbent article according to an eighth embodiment, wherein FIG. 9a shows the lateral side portion in an intermediate manufacturing state of the article, and FIG. 9b shows a final configuration of the lateral side portion.

FIGS. 10a and 10b are cross sectional views of a lateral side portion of an absorbent article according to a ninth embodiment, wherein FIG. 10a shows the lateral side portion in an intermediate manufacturing state of the article, and FIG. 10b shows a final configuration of the lateral side portion.

FIGS. 11a and 11b are cross sectional views of a lateral side portion of an absorbent article according to a tenth embodiment, wherein FIG. 11a shows the lateral side portion in an intermediate manufacturing state of the article, and FIG. 11b shows a final configuration of the lateral side portion.

FIGS. 12a and 12b are cross sectional views of a lateral side portion of an absorbent article according to an eleventh embodiment, wherein FIG. 12a shows the lateral side portion in an intermediate manufacturing state of the article, and FIG. 12b shows a final configuration of the lateral side portion.

FIGS. 13a and 13b are cross sectional views of a lateral side portion of an absorbent article according to the prior art, wherein FIG. 13a shows the lateral side portion in an intermediate manufacturing state of the article, and FIG. 13b shows a final configuration of the lateral side portion.

DETAILED DESCRIPTION OF PREFERRED EMBODIMENTS

Figure 1:
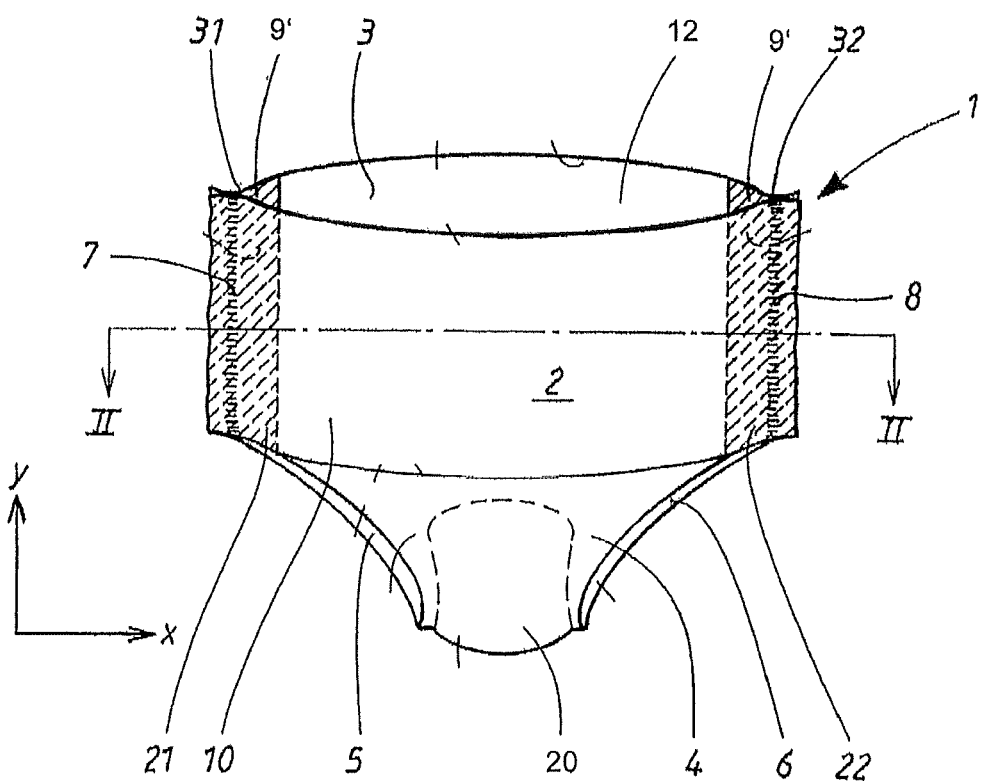
FIG. 1 is a perspective view of a pants-type diaper according to the present disclosure, the lateral side portions of which are constituted according to any one of the embodiments shown in FIGS. 2b through 12b.

FIG. 1 shows hygiene pants in the form of diaper pants 1 for children or incontinent adults. The diaper pants 1 have a front part 2, a back part 3 and a crotch portion 4 there between. In use, the front part 2 is located on the wearer's abdomen, whereas the back part 3 is located on the wearer's back. The crotch portion 4 in the present case is welded to the front and back parts 2, 3 and includes an absorption unit 20. The crotch portion 4 may generally also be integral with the front and back parts, or connected thereto by means other than welding.

The diaper pants have a transverse direction, which in FIG. 1 is marked with x, and a longitudinal direction, which is marked with y, and which is also the machine direction of the production process in most cases, although there can be a cross directional direction in some instances.

The lateral side portions 21 and 22 of the front part 2, as seen in the transverse direction, are connected by welded side seams 7 and 8 to the lateral side portions 31 and 32 of the back part 3, as seen in the transverse direction, in order to form leg openings 5, 6 as well as a waist opening 12.

The lateral side portions 21, 22, 31, 32 of the front part 2 and the back part 3 of the hygiene pants may comprise one layer or two or more layers that have been laminated. In general terms, each of the lateral side portions 21, 22, 31, 32 could be constituted by a single non-woven material layer. In the illustrative embodiment shown in FIG. 1, however, a laminate 10 is provided for the lateral side portions of both the front part 2 and the back part 3 of the diaper pants 1. The laminate 10 generally includes an elastic film which is sandwiched between two nonwoven layers. More particularly, the laminate 10 may include a non-woven backsheet, an elastic film, and a non-woven standing-gather web which are superposed onto each other. (Note that in the present context, a "standing-gather web" is a material layer which is used for forming standing gathers in the absorbent article.)

In the areas of the side seams 7 and 8, the laminates 10 of the lateral side portions of the front part 2 and the back part 3 are superposed onto and connected with each other. In this context, it is important to bear in mind that hygiene pants of the type discussed here are subjected to considerable stresses when being put on. The hygiene pants are stretched and the welded side seams are exposed to considerable stresses.

In general terms, the strength of the side seam, which is important for the function of the product, strongly depends on the type of non-woven materials used and the CD (cross directional) strength of the raw materials. Non-wovens may vary considerably regarding their CD strength and their base weight variations.

In the prior art, such side seams 7, 8 have for example been formed by mechanical welding. FIGS. 13*a* and 13*b* show a corresponding prior art embodiment. In these Figures as well as in FIGS. 2*a* through 12*b* which will be discussed further below, reference numeral 2 designates the front part of the diaper, reference numeral 3 designates the back part, and these portions 2, 3 are delimited against each other by means of a broken line.

From FIG. 13*a* it becomes clear that the pant diaper is constituted by a total of six layers in the areas of the side seams 7 and 8: the non-woven backsheets 13, the elastic films 11, and the non-woven standing-gather webs 9 of the lateral side portions of both the front 2 and the back parts 3 are superposed onto each other. In other words, the lateral side portions of both the front part 2 and the back part 3 have two non-woven layers 9, 13 and an elastic film 11 there between. The respective outer non-woven layer is the back sheet 13, and the respective inner non-woven layer is the standing-gather web 9.

Subsequent to the welding, the outermost parts of the material layers 9, 11 and 13 are cut away along a longitudinal cutting line running close to the side seam 7, 8. The course of the cutting line CL is indicated by a dot and dash line in FIG. 13*a*. FIG. 13*b* shows the side seam of the diaper after the cutting operation.

When it comes to the side seam strength, in particular the peel strength of the side seams, an important area is the area close to the side seams. Furthermore, the non-woven standing gather web 9 contributes most to the side seam strength. From a cost saving perspective it would be desirable to lower the grammage of the standing gather web 9. However, if the grammage is reduced to below a certain level, the CD strength is also reduced, and the required seam strength cannot be obtained any more.

The present disclosure provides the possibility to reduce the grammage of the non-woven layer 9 while still obtaining the required seam strength. To this extent, reinforcement of the side seams 7, 8 is provided by reinforcing the non-woven layer 9 in the areas of the side seams 7, 8.

The present disclosure provides several different possibilities for reinforcing the non-woven layer 9 in the areas of the side seams 7, 8. These possibilities will now be discussed with reference to the embodiments shown in FIGS. 2*a* to 12*b*.

In any of FIGS. 2*a* through 12*b*, the cross section is taken along the line II-II in FIG. 1. The Figures are, however, very schematic and intended to mainly illustrate the superposition of the individual layers and in particular the manner in which the standing-gather web 9 is folded in each individual case. In reality, the layers would of course be disposed much more closely together after the side seams 7, 8 have been formed. Furthermore, the individual layers 9, 11 and 13 of the lateral side portions are illustrated by different types of lines which have been chosen so as to distinguish the layers from each other rather than to allow a conclusion as to the properties of the individual layers. For example, although the layer 9 is illustrated by means of a thicker line than the layer 13, this does not necessarily mean that the layer 13 is thicker than the layer 9. The elastic film 11 is illustrated by means of a broken line, but this does not necessarily mean that the film 11 is perforated.

According to a first alternative, the reinforcement is obtained by providing an additional layer of nonwoven material which extends at least in the areas of the side seam. This additional layer of nonwoven material may in turn be obtained by folding the non-woven material layer 9 of the lateral side portions of the front part 2 and/or the back part 3 upon itself along the opposing longitudinal side edges of the layer 9.

In the presently preferred embodiments, the non-woven material layer which is folded is the standing gather web 9.

FIGS. 2*a* through 7*b* illustrate several different possibilities for obtaining this additional layer of nonwoven material by folding.

FIGS. 2*a* and 2*b* show one of the lateral side portions of a diaper according to a first embodiment. Similar as in the prior art just described with reference to FIGS. 13*a* and 13*b*, the lateral side portions of the front and back parts 2, 3 of the diaper are superposed onto each other and joined by means of side seams, only one of which (8) is schematically illustrated in the Figures. In contrast to the prior art, however, reinforcement of the side seam 8 is provided by the provision of two additional layers 9' of web material, which in this case are formed by folding the non-woven standing gather webs 9 of both the front part 2 and the back part 3 upon themselves. The folding is done so that the fold line is substantially aligned with the longitudinal direction (y) of the diaper.

In the present embodiment, the nonwoven layers 9 are folded so that the additional layers 9', i.e. the folded side margins, come to be positioned between the respective elastic film 11 and the respective standing gather web 9. The additional material layer 9' is therefore placed in between the layers 9 and 11 of the laminate. In the resultant product, the additional layer 9' is not visible when regarding the side seams 7, 8 from inside the final product.

The resultant folded portions may have a width in the x-direction (perpendicular to the longitudinal direction y) of about 20 mm to about 40 mm.

In FIG. 1, the areas where the nonwoven layers 9 are reinforced are also schematically indicated by hatching.

Note that the outermost parts of the material layers 9, 9', 11 and 13 are required for handling and guiding the material during the individual manufacturing process steps, including the welding step. Subsequent to the welding, however, the outermost parts of the material layers 9, 9', 11 and 13 are cut away along a longitudinal cutting line running close to the side seam 7, 8. The course of the cutting line CL is indicated by a dot and dash line in FIG. 2a. FIG. 2b shows the lateral side portion of the diaper after the cutting operation.

The side seams 7, 8 may be formed by ultrasonic welding, mechanical welding, thermo-mechanical welding, or still another bonding method.

FIGS. 3a and 3b show a diaper according to a second embodiment in the area of one of its side edges. In this embodiment, reinforcement of the ultrasonic weld seams 7, 8 is provided by only one additional layer 9' of web material which in this case are formed by folding the non-woven standing gather web 9 of only the front part 2 upon itself. As an alternative, the single additional layer 9' could be provided by folding the longitudinal edge of the non-woven standing gather web 9 of only the back part 3 upon itself.

FIG. 3b shows the lateral side portion of the diaper after cutting away the outermost parts of the material layers 9, 9', 11 and 13.

Figures 4A, 4B:
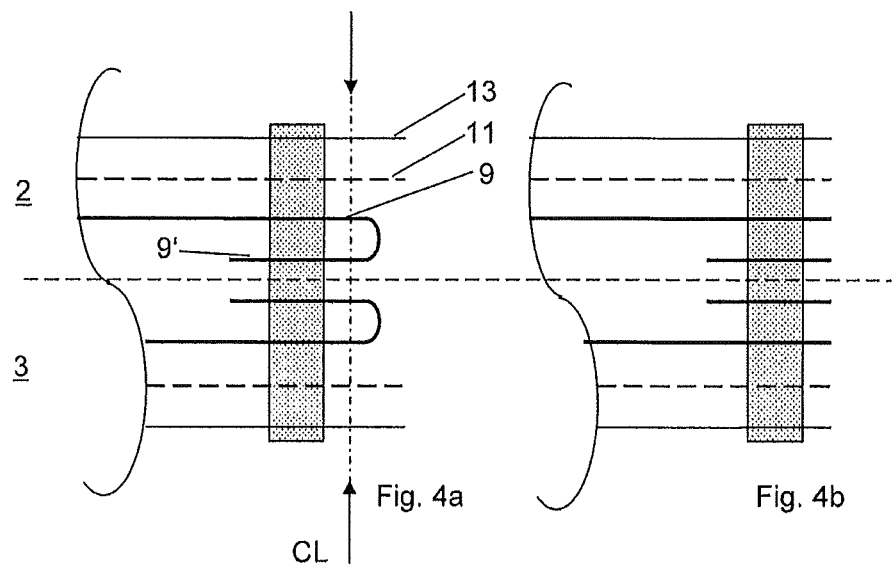

FIGS. 4a and 4b show a diaper according to a third embodiment in the area of one of its lateral side portions. This embodiment is the same as the first embodiment shown in FIGS. 2a and 2b, except that the longitudinal edges of the non-woven standing gather webs 9 are folded in the opposite direction so that the additional layers 9' face each other rather than facing the elastic films 11.

FIG. 4b shows the lateral side portion of the diaper after cutting away the outermost parts of the material layers 9, 9', 11 and 13.

Figures 5A, 5B:
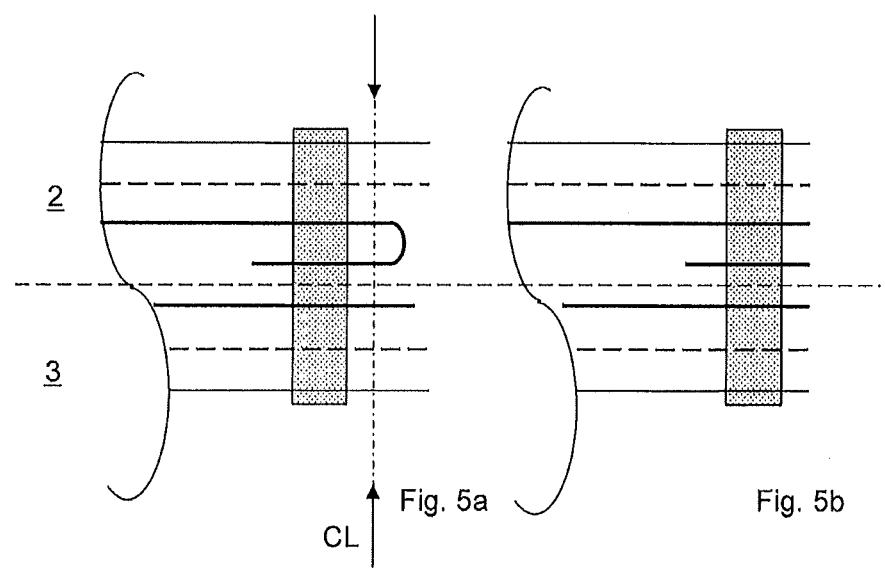

FIGS. 5a and 5b show a diaper according to a fourth embodiment in the area of one of its lateral side portions. This embodiment is the same as the second embodiment shown in FIGS. 3a and 3b, except that the longitudinal edge of the non-woven standing gather web 9 is folded in the opposite direction so that the additional layer 9' formed on the front part 2 faces the non-woven standing gather web 9 of the back part 3 rather than facing the elastic film 11.

FIG. 5b shows the lateral side portion of the diaper after cutting away the outermost parts of the material layers 9, 9', 11 and 13.

FIGS. 6a and 6b show a diaper according to a fifth embodiment in the area of one of its lateral side portions. In this case, reinforcement of the ultrasonic weld seam 7, 8 is provided by four additional layers 9', 9'' of web material which are formed by double folding the longitudinal edges of the non-woven standing gather webs 9 of both the front part 2 and the back part 3 upon themselves. The longitudinal edges are folded so that the additional layers 9', 9'' come to be positioned between the respective elastic film 11 and the respective standing gather web 9.

FIG. 6b shows the lateral side portion of the diaper after cutting away the outermost parts of the material layers 9, 9', 9'', 11 and 13.

FIGS. 7a and 7b show a diaper according to a sixth embodiment in the area of one of its lateral side portions. In this embodiment, reinforcement of the ultrasonic weld seam 7, is provided by only two additional layers 9', 9'' of web material which are formed by double folding the longitudinal edge of the non-woven standing gather web 9 of only the front part 2 upon itself. As an alternative, the two additional layers 9', 9'' could be provided by double folding the longitudinal edge of the non-woven standing gather web 9 of only the back part 3 upon itself.

FIG. 7b shows the lateral side portion of the diaper after cutting away the outermost parts of the material layers 9, 9', 11 and 13.

Note that the folding could also be done in the opposite direction such that the additional layers 9', 9'' are positioned towards the inside of the multi-layer arrangement.

In all of the embodiments of the present disclosure, the non-woven layer or layers of the lateral side portions 21, 22, 31, 32 is or are intended to provide softness and a textile feel. Examples of suitable materials are carded nonwovens and spunbond nonwovens. Examples of suitable fibre materials such as polyethylene and polypropylene are indicated in the abovementioned patent applications.

In the above embodiments which use the outer non-woven fibre layers 9, 13 and the elastic film 11 in the laminate 10, it is preferred that the non-woven backsheet 13 and the non-woven standing gather web 9 are chosen so that they, in combination with the elastic film 11 provided there between, give the material high resistance to puncture.

The backsheet 13 may be made from a liquid impervious material. The backsheet 13 may be breathable so as to allow vapour to escape from the absorbent core, while still preventing liquids from passing therethrough. Examples of breathable backsheet materials are nonwoven laminates from spunbond and meltblown layers. The backsheet 13 as such is preferably inelastic.

According to a specific example, nonwoven backsheets 13 having a grammage of 18 $g/m^2$ or 14 $g/m^2$ or bicomponent nonwoven backsheets 13 having a grammage of 14 $g/m^2$ could be used in combination with non-woven standing gather webs 9 having a grammage of 14 $g/m^2$, as long as they are reinforced in the areas of the side seams 7, 8 in accordance with the present disclosure.

The elastic film 11, which, in the present embodiment, is provided in the laminate 10 between the two non-woven layers 9 and 13, is expediently perforated so that the cover is made permeable to air and vapour.

The grammage of the elastic film is expediently between 20 and 100 $g/m^2$, preferably between 20 and 60 $g/m^2$. The film may be of any suitable elastic polymer, natural or synthetic. Some examples of suitable materials for the elastic film are low crystallinity polyethylenes, metallocene-catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymers. Blends of these polymers may also be used as well as other modifying elastomeric or non-elastomeric materials.

One example of a suitable film is an apertured three-layer elastomeric film of PE-SEBS-PE. According to another example, the elastic film 11 may be a three-ply film 11 of PO-SIS-PO provided with holes and having a grammage of 47 g/m². Further suitable examples of materials and material combinations for the elastic film are indicated in abovementioned patent applications WO 2005/122984 A1 and WO 2005/122985 A1.

In particular if the side seams 7, 8 are formed by ultrasonic welding, the standing-gather web 9 and/or the backsheet 13 can also be made from a bicomponent non-woven material, combining the benefits and characteristics from two different polymers within the web. The ultrasonic welding of such materials is facilitated by the folding of the non-woven layer upon itself and the additional material obtained thereby in the areas of the side seams.

The folding of the standing gather web 9 along the longitudinal side edges is a process step which can be easily implemented into existing product lines. If compared with, for example, the feeding of an additional strip of non-woven material upon welding the side seams, the process efficiency is enhanced. Providing the additional nonwoven material layer in the form of separate nonwoven strips would in turn have the advantage that the choice of material is wider, because the additional material layer should not necessarily be the same material as the nonwoven layer or standing gather web 9, respectively.

FIGS. 8a through 12b illustrate further embodiments, wherein the respective Figure "a" shows the lateral side portion of the article prior to the cutting step, while the respective Figure "b" shows the lateral side portion in the final condition, i.e. after the outermost marginal areas outside of the side seams have been removed by cutting.

FIGS. 8a and 8b show an embodiment which does not use any elastic film in the areas of the side seams 7, 8. While an elastic film 11 is provided as part of the laminate 10 which constitutes the lateral side portions 21, 22, 31, 32 of the front part 2 and the back part 3, the film 11 does not extend into the area of the side seams 7, 8. In other words, only the non-woven backsheets 13 and the non-woven standing gather webs 9 as well as the additional nonwoven layers 9' of the front part 2 and the back part 3 are connected by means of the side seams, while the elastic films 11 of the front part 2 and the back part 3 terminate inward of the side seams 7, 8.

In order to reinforce the side seam, the standing gather web 9 has been folded upon itself so as to provide the additional material layer 9', similar as in the above embodiment of FIGS. 2a and 2b. In fact, the embodiment of FIGS. 8a and 8b is the same as the one of FIGS. 2a and 2b apart from the fact that the elastic film 11 is not present in the areas where the side seams 7, 8 are formed.

In the embodiment of FIGS. 9a and 9b, no such folding of the standing gather web 9 upon itself is effected, but the additional layer 9' of nonwoven material is provided by placing an additional strip of material between the nonwoven layer 9 and the nonwoven layer 13.

The embodiment of FIGS. 10a and 10b is similar to the embodiment of FIGS. 8a and 8b, but the nonwoven layer 9 has been folded upon itself so that the additional layers 9' face each other, rather than facing the backsheets 13 as it is the case in FIGS. 8a and 8b.

The embodiment of FIGS. 11a and 11b is the same as the one of FIGS. 10a and 10b, but uses separate strips of nonwoven material in order to constitute the additional layers 9'.

Note that in all the embodiments of FIGS. 8 through 11, the additional layer of material could also be present on only one of the two parts of the product, i.e. only the front part, as it is the case in FIGS. 3, 5 and 7, or only the back part.

Furthermore, in all the embodiments of FIGS. 8 through 11, there could also be more than one additional layer of material, e.g. two additional layers 9', 9" like in FIGS. 6 and 7.

Moreover, in all the embodiments of FIGS. 8 through 11, neither the elastic film 11 of the front part 2 nor the elastic film 11 of the back part 3 extends into the area of the side seams 7, 8, so that only the nonwoven layers 9, 9' and 13 of the front part 2 and the back part 3 are connected by means of the side seams 7, 8. It is, however, also possible to provide such a configuration only on the front part 2 or only on the back part 3, while the respective other part of the diaper has an elastic film 11 which does extend into the area of the side seams 7, 8. The side seams 7, 8 would then, for example, connect the nonwoven layers 9, 9' and 13 of the front part 2 with the nonwoven layers 9, 9', 13 and the elastic film 11 of the back part 3.

Finally, FIGS. 12a and 12b show an embodiment in which the reinforcement of the side seam is not done by providing an additional layer of material but by reinforcing the nonwoven layer 9 in the area where the side seam is provided. Strips of material 9''', which have a higher grammage than the actual nonwoven layer 9, are connected to the longitudinal side edges of the nonwoven layer 9. This connection can, for example, be done by mechanical welding or ultrasonic welding. The connection can be a butt joint or, as shown in FIGS. 12a and 12b, be effected with a slight overlap.

In the embodiment of FIG. 12, at least either the front part 2 or the back part 3 could also dispense with the elastic film in the areas of the side seams 7, 8, as explained above with reference to FIGS. 8 to 11.

Alternatively or in addition to increasing the grammage of the material in the area of the side seam 8, the strength of the material, in particular the cross directional (CD) strength, could also be increased. In other words, the strips of material 9''' in FIGS. 12a and 12b have a higher grammage and/or a higher strength, in particular cross directional strength, than the remainder of the nonwoven layer 9.

The reinforcement of the nonwoven layer of material, in the above embodiments the standing gather web 9, has a positive influence on the strength of the side seams 7, 8. Even if the grammage of the material layer 9 as such is reduced, the required side seam strength is reliably achieved. At the same time, costs are saved due to the lower grammage of the layer 9.

For example, by using a low grammage standing-gather web (14 g/m²) and reinforcing it by folding it in the areas of the side seams, a seam strength is obtained which is comparable with that of an embodiment using higher grammage standing-gather web (18 g/m²). This means that the grammage of the standing-gather web 9 can be reduced to as low as 14 g/m² while the required seam strength is still achieved. The seam strength would still be sufficient if the grammage of the standing-gather web 9 would be further reduced to about 10 g/m². Such a reduction to 10 g/m² will be particularly possible for rather homogeneous nonwovens, so as to provide the required cross directional strength.

Apart from the saving of costs, the reduced grammage of the standing gather web 9 also leads to the product being softer in perception.

The grammage of the backsheet 13 can also be reduced while the required seam strength is still achieved. This is because the reinforcement of the nonwoven standing gather web 9 by e.g. providing the additional material layer(s) 9', 9"

compensates for the reduced grammage also of the backsheet 13 in the areas of the side seams 7, 8.

It should be understood that, although preferred embodiments have been described, modifications are possible within the scope of the claims.

For example, in the embodiments illustrated in FIGS. 2a to 7b, the cutting of the outer longitudinal edge portions of the front part 2 and the back part 3 after welding the side seams is done so that the folded portions of the standing gather webs 9 are cut away. The folding could, however, also be effected further towards the side seams 7, 8 (see dotted lines in FIGS. 6a and 6b) so that the folded portions are not affected by the cutting. In this manner the amount of material which is cut away can be reduced.

Furthermore, the above embodiments of FIGS. 2a to 11b use one 9' or two additional layers 9', 9" in the areas of the side seams 7, 8. In accordance with the present disclosure, it would generally be possible to provide three or even more additional layers, e.g. by corresponding further folding actions of the non-woven layer 9. The side seams 7, 8 will then become considerably stronger than the material adjacent the seams.

Moreover, in any one of FIGS. 2a to 12b, only one (8) of the two side seams 7, 8 of the diaper is shown. In most cases, both side seams 7, 8 of the diaper will also have the same configuration. However, in the frame of the present disclosure, it is generally also possible to have a diaper in which the side seams 7 and 8 have different configurations. In particular, there could be a case in which the elastic film 11 of the front part 2 and/or the back part 3 extends into the area of one of the side seams 7, 8 whereas it terminates inward of the other one of the side seams. In more general terms, a hygienic article of the present disclosure could have only one of the two side seams configured in accordance with the present disclosure.

Finally, it is also envisaged to use combinations of the above embodiments: for example, additional reinforcing non-woven strips of nonwoven material could be used in combination with additional material layers obtained by folding.

What is claimed is:

1. A method of manufacturing an absorbent article, the method:
    providing a blank for said absorbent article, the blank comprising a front part, a back part, and a crotch part between the front part and the back part, wherein each of the front part and back part has lateral side portions,
    superposing the lateral side portions of the front part and the back part, so that an inner surface of the lateral side portions of the front part directly contact an inner surface of the lateral side portions of the back part, and directly joining the lateral side portions of the front part to the lateral side portions of the back part to form side seams extending in a longitudinal direction of the absorbent article, wherein,
    wherein the lateral side portions of at least one of the front part and the back part include a first layer of nonwoven material which has been reinforced, before the superpositioning, in an area where at least one of the side seams is formed,
    the reinforced portions are reinforced by folding the first layer of nonwoven material upon itself to provide at least one additional layer of nonwoven material extending at least in the area of the at least one side seam.

2. The method of claim 1, wherein the at least one additional layer of nonwoven material is laminated to the first layer of nonwoven material prior to the superposing of the lateral side portions of the front part and the back part.

3. The method of claim 1, wherein the first layer of nonwoven material is folded upon itself about a fold line extending essentially in the longitudinal direction of the absorbent article.

4. The method according to claim 1, wherein the first layer of nonwoven material is double folded upon itself to provide the at least one of the side seams with at least two additional layers of material.

5. The method of claim 1, wherein the at least one additional layer of material is provided on an outer surface of the first layer of nonwoven material.

6. The method of claim 1, further including providing the lateral side portions of at least one of the front part and the back part with an elastic film which does not extend to where the at least one side seam is formed.

7. The method of claim 1, wherein the side seams are formed by ultrasonic welding.

8. The method according to claim 1, further including cutting away parts of the lateral side portions of the absorbent article beyond the side seams.

9. The method of claim 1, wherein the at least one additional layer of nonwoven material extends at least in the area of the at least one side seam along an entire length of the side seam.

10. The method of claim 1, wherein the at least one additional layer of nonwoven material extends at least in the area of the at least one side seam, wherein the at least one additional layer of nonwoven material has a width in a direction perpendicular to the longitudinal direction of less than or equal to 40 mm.

11. The method of claim 1, wherein the inner surface of the lateral side portions is the first layer of nonwoven material.

* * * * *